US010888302B2

(12) United States Patent
Honma

(10) Patent No.: US 10,888,302 B2
(45) Date of Patent: *Jan. 12, 2021

(54) IMAGE PROCESSING DEVICE, METHOD, AND PROGRAM

(71) Applicant: TERUMO KABUSHIKI KAISHA, Tokyo (JP)

(72) Inventor: Yasuyuki Honma, Kanagawa (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 16/738,481

(22) Filed: Jan. 9, 2020

(65) Prior Publication Data

US 2020/0151949 A1 May 14, 2020

Related U.S. Application Data

(63) Continuation of application No. PCT/JP2018/025381, filed on Jul. 4, 2018.

(30) Foreign Application Priority Data

Jul. 12, 2017 (JP) ................................. 2017-136534
Jul. 12, 2017 (JP) ................................. 2017-136537

(51) Int. Cl.
*A61B 5/044* (2006.01)
*G06T 3/00* (2006.01)
(Continued)

(52) U.S. Cl.
CPC ............ *A61B 8/461* (2013.01); *A61B 5/0044* (2013.01); *A61B 5/044* (2013.01); *A61B 5/055* (2013.01);
(Continued)

(58) Field of Classification Search
CPC .... G06T 3/0031; A61B 5/0073; A61B 5/0044
See application file for complete search history.

(56) References Cited

U.S. PATENT DOCUMENTS 6,160,924 A * 12/2000 Lazar ...................... G06T 15/00
382/276
2009/0177089 A1* 7/2009 Govari .................. A61B 8/543
600/453

(Continued)

FOREIGN PATENT DOCUMENTS

JP  2005-058535 A  3/2005
JP  2008-167802 A  7/2008

(Continued)

OTHER PUBLICATIONS

International Preliminary Report on Patentability (Including Translation) for International Application No. PCT/JP2018/025381, dated Jan. 14, 2020.

(Continued)

*Primary Examiner* — Phi Hoang
(74) *Attorney, Agent, or Firm* — Thaine Lennox-Gentle; Sheridan Ross, PC

(57) ABSTRACT

An image processing device is described herein including an information input unit that receives as an input three-dimensional structure information indicating a three-dimensional structure of a heart; and an image generation unit that develops an inner wall of atria and ventricles of a heart indicated by the three-dimensional structure information into a two-dimensional image based on an equal-area projection, and generates a developed image interrupted by dividing the two-dimensional image into a front wall, a rear wall, a left wall, and a right wall.

20 Claims, 9 Drawing Sheets

(51) Int. Cl.
- *A61B 8/00* (2006.01)
- *A61B 5/00* (2006.01)
- *A61B 5/055* (2006.01)
- *A61B 6/03* (2006.01)
- *A61B 6/00* (2006.01)
- *A61B 8/08* (2006.01)
- *A61B 8/14* (2006.01)

(52) U.S. Cl.
CPC ............. *A61B 5/742* (2013.01); *A61B 6/037* (2013.01); *A61B 6/461* (2013.01); *A61B 6/503* (2013.01); *A61B 8/0883* (2013.01); *A61B 8/145* (2013.01); *G06T 3/0037* (2013.01); *G06T 2200/08* (2013.01)

(56) References Cited

U.S. PATENT DOCUMENTS

| | | | |
|---|---|---|---|
| 2015/0173707 A1 | 6/2015 | Ohuchi et al. | |
| 2017/0199654 A1* | 7/2017 | Wu | A61B 5/055 |
| 2017/0209059 A1* | 7/2017 | Nabutovsky | A61B 5/1102 |
| 2019/0318534 A1* | 10/2019 | Mory | A61B 8/4483 |
| 2020/0151850 A1 | 5/2020 | Honma | |

FOREIGN PATENT DOCUMENTS

| | | |
|---|---|---|
| JP | 2011-123045 A | 6/2011 |
| JP | 2015-119768 A | 7/2015 |

OTHER PUBLICATIONS

International Search Report for International Application No. PCT/JP2018/025381, dated Sep. 25, 2018.
Written Opinion for International Application No. PCT/JP2018/025381, dated Sep. 25, 2018.
International Preliminary Report on Patentability for International Application No. PCT/JP2018/025381, dated Jan. 14, 2020.
International Search Report for International Application No. PCT/JP2018/025380, dated Sep. 25, 2018.
Written Opinion for International Application No. PCT/JP2018/025380, dated Sep. 25, 2018.
International Preliminary Report on Patentability for International Application No. PCT/JP2018/025380, dated Jan. 14, 2020.
Office Action for U.S. Appl. No. 16/738,568, dated Jun. 11, 2020.
Notice of Allowance for U.S. Appl. No. 16/738,568, dated Sep. 15, 2020.

* cited by examiner

IMAGE PROCESSING DEVICE, METHOD, AND PROGRAM

CROSS REFERENCE TO RELATED APPLICATIONS

The present application is a continuation of and claims benefit to PCT application No. PCT/JP2018/025381, filed on Jul. 4, 2018, entitled "IMAGING PROCESSING DEVICE, IMAGE PROCESSING METHOD, AND PROGRAM" which claims priority to Japanese Patent Application No. 2017-136534, filed on Jul. 12, 2017, and Japanese Patent Application No. 2017-136537, filed on Jul. 12, 2017. The entire disclosures of the applications listed above are hereby incorporated herein by reference, in their entirety, for all that they teach and for all purposes.

FIELD

The present disclosure relates to an image processing device, an image processing method, and a program.

BACKGROUND

In treatments of heart failure or the like, studies have been conducted regarding a treatment in which a treatment effect is expected by injecting a biological substance such as a cell or a material to be administered such as a biomaterial is injected into tissues around atria and ventricles (for example, a myocardium around the left ventricle) using a tool such as a catheter inserted into the atria and ventricles of the heart through a femoral artery or the like. In addition, as a treatment for arrhythmia and the like, there is an ablation treatment in which a region that causes arrhythmia is cauterized by a catheter inserted into atria and ventricles of a heart.

In the treatment described above, a position of a region of interest, such as an infarcted region, where a myocardium is necrotized due to occlusion or stenosis of a coronary artery is identified based on data obtained by an X-ray tomography device, a magnetic resonance imaging device, and the like. Further, a two-dimensional or three-dimensional image of the heart including the identified region is generated and displayed. For example, Japanese Patent Application No. JP 2015-119768 A discloses a technique for two-dimensionally mapping three-dimensional cardiac function information indicating local motion information of a myocardium and a three-dimensional shape of a coronary artery on a bull's eye map. In addition, Japanese Patent Application No. JP 2008-167802 A discloses a technique for two-dimensionally developing the entire surface of a heart wall using the Goode projection and forming a two-dimensional surface image of the heart wall interrupted while avoiding a coronary artery of the heart on the developed view.

SUMMARY

Technical Problem

In the treatments described above, it is necessary to intuitively and accurately grasp a state of an inner wall of the heart in order to accurately identify a region of interest such as an infarct region and a treatment region (an injection region of a material to be administered). Here, the bull's eye map is an image obtained by projecting three-dimensional data in a plurality of uniaxial sections perpendicular to a major axis direction from a cardiac base to a cardiac apex on a circle whose center corresponds to the cardiac apex and whose edge corresponds to the cardiac base. In the bull's eye map, it is difficult to accurately express the length and area. Therefore, it is difficult to intuitively and accurately grasp the state of the heart in the technique disclosed in Japanese Patent Application No. JP 2015-119768 A because the length and area are not accurately expressed. In addition, since the development view of the entire surface of the heart wall two-dimensionally developed according to the Goode projection is interrupted while avoiding the coronary artery in the technique disclosed in Japanese Patent Application No. JP 2008-167802 A, the relationship between a shape after the interruption and the entire surface of the heart wall becomes complicated, and the intuitive grasping is difficult. In addition, the technique disclosed in Japanese Patent Application No. JP 2008-167802 A expresses the entire surface of the heart wall two-dimensionally, and there is no consideration on how to intuitively and accurately grasp the state of the inner wall of the atria and ventricles of the heart.

An object of the present disclosure is to provide an image processing device, an image processing method, and a program that can solve the above-described problems and can intuitively and more accurately grasp a state of an inner wall of a heart.

Solution to the Problem

An image processing device as a first aspect of the present disclosure includes: an information input unit that receives as an input three-dimensional structure information indicating a three-dimensional structure of a heart; and an image generation unit that develops an inner wall of atria and ventricles of the heart indicated by the three-dimensional structure information into a two-dimensional image based on an equal-area projection and generates a developed image interrupted by dividing the two-dimensional image into a front wall, a rear wall, a left wall, and a right wall of the inner wall.

As one embodiment of the present disclosure, the image generation unit makes a mode of a region of interest in the heart different from a mode of another region on the developed image.

As one embodiment of the present disclosure, the information input unit receives as an input time-series three-dimensional structure information including diastole and systole of the heart, and the image generation unit generates the developed image for each of the diastole and the systole based on the time-series three-dimensional structure information.

As one embodiment of the present disclosure, the region of interest is an infarcted region of the heart, and the image generation unit corrects a position of the region of interest based on a developed image in the diastole and a developed image in the systole.

As one embodiment of the present disclosure, the image generation unit identifies a position of a heart valve based on the three-dimensional structure information, and maps the identified heart valve on the developed image.

As one embodiment of the present disclosure, the image generation unit displays an open/closed state of the heart valve on the developed image.

As one embodiment of the present disclosure, the image generation unit obtains a wall thickness of the inner wall based on the three-dimensional structure information, and maps the obtained wall thickness on the developed image.

As one embodiment of the present disclosure, the information input unit further receives as an input electrocardiogram information indicating an electrocardiogram of the inner wall, and the image generation unit maps the electrocardiogram of the inner wall on the developed image based on the electrocardiogram information.

As one embodiment of the present disclosure, the image generation unit acquires a wall motion state of the inner wall based on the three-dimensional structure information, and maps the acquired wall motion state on the developed image.

As one embodiment of the present disclosure, the information input unit further receives as an input electrocardiogram information indicating an electrocardiogram of the inner wall, and the image generation unit identifies a region where the wall motion state of the inner wall and the electrocardiogram of the inner wall satisfy predetermined conditions, and maps the identified region on the developed image.

As one embodiment of the present disclosure, an operation input unit that receives an operation input is further provided, and the image generation unit displays the generated developed image on a display unit, and displays a marker indicating a position given in instruction by an operation input on the developed image in a superimposed manner when the operation input unit receives the operation input giving an instruction on the position on the developed image displayed on the display unit.

As one embodiment of the present disclosure, an operation input unit that receives an operation input is further provided, and the image generation unit displays the generated developed image on a display unit, obtains a wall thickness of the inner wall based on the three-dimensional structure information, and displays the wall thickness at a position given in instruction by an operation input on the display unit when the operation input unit receives the operation input giving an instruction on the position on the developed image displayed on the display unit.

An image processing method as a second aspect of the present disclosure is an image processing method, which is executed using an image processing device, and includes: a step of receiving as an input three-dimensional structure information indicating a three-dimensional structure of a heart; and a step of developing an inner wall of atria and ventricles of the heart indicated by the three-dimensional structure information into a two-dimensional image based on an equal-area projection and generating a developed image interrupted by dividing the two-dimensional image into a front wall, a rear wall, a left wall, and a right wall of the inner wall.

As one embodiment of the present disclosure, the image processing method further includes a step of identifying a position of a heart valve based on the three-dimensional structure information and mapping the identified heart valve on the developed image.

A program as a third aspect of the present disclosure causes a computer to function as any one of the image processing devices described above.

Non-Exhaustive Advantages

With the image processing device, the image processing method, and the program according to the present disclosure, it is possible to intuitively and more accurately grasp, or understand, the state of the inner wall of the heart.

DETAILED DESCRIPTION

Hereinafter, embodiments of the present disclosure will be described with reference to the drawings.

Figure 1:
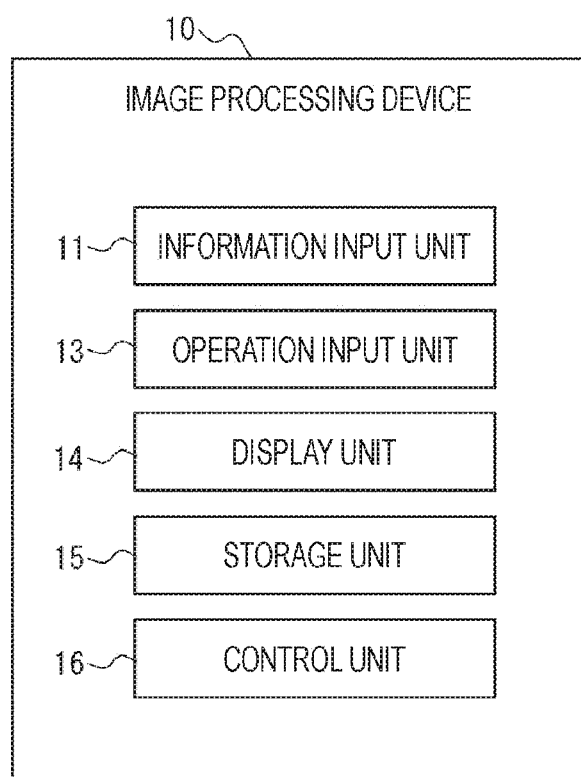
FIG. 1 is a diagram illustrating a configuration example of an image processing device according to one embodiment of the present disclosure.

FIG. 1 is a diagram illustrating a configuration example of an image processing device 10 according to an embodiment of the present disclosure. The image processing device 10 according to the present embodiment generates and displays an image in which an inner wall of a heart of a subject is developed two-dimensionally.

The image processing device 10 illustrated in FIG. 1 is located outside a body of the subject and is configured using an information processing device such as a computer. The image processing device 10 includes an information input unit 11, an operation input unit 13, a display unit 14, a storage unit 15, and a control unit 16. The control unit 16 is an example of an image generation unit.

The information input unit 11 receives as an input three-dimensional structure information indicating a three-dimensional structure of the heart of the subject. The information input unit 11 receives as an input information, as the three-dimensional structure information, indicating the three-dimensional structure of the heart obtained by, for example, a computed tomography (CT) device, a magnetic resonance imaging (MRI) device, a three-dimension ultrasonography (3D-US) device, or the like. The information input unit 11 includes an interface that receives the information from these devices by, for example, wired communication or wireless communication. The information input unit 11 outputs the input information to the control unit 16.

The operation input unit 13 receives an operation input from a user. The operation input unit 13 includes, for example, a keyboard, a mouse, a touch panel, and/or the like. When the operation input unit 13 includes a touch panel, the touch panel may be provided integrally with the display unit 14. The operation input unit 13 outputs a signal corresponding to an input operation to the control unit 16.

The display unit 14 displays an image generated by the control unit 16 according to the control of the control unit 16. The display unit 14 includes a display device such as a liquid crystal display and an organic electro luminescence (EL) display.

The storage unit 15 stores various types of information and programs configured to cause the control unit 16 to execute a specific function. Further, the storage unit 15 stores, for example, an image generated by the control unit 16 to be described later. The storage unit 15 includes, for example, a storage device such as a random access memory (RAM) device and a read only memory (ROM) device.

The control unit 16 controls an operation of each component that constitutes the image processing device 10. The control unit 16 executes a specific function by reading a specific program. Specifically, the control unit 16 develops or maps the inner wall of the atria and ventricles (the left atrium, the right atrium, the left ventricle, and the right ventricle) of the heart indicated by the three-dimensional structure information acquired by the information input unit 11 based on an equal-area projection, and generates a developed image interrupted by dividing the two-dimensional image into a front wall, a rear wall, a left wall, and a right wall of the inner wall. The control unit 16 displays the generated developed image on the display unit 14 and also stores the developed image in the storage unit 15. The control unit 16 includes a processor, for example.

Next, the generation of the developed image by the control unit 16 will be described in more detail.

The control unit 16 develops or maps the inner wall of the atria and ventricle of the heart of the subject indicated by the three-dimensional structure information into the two-dimensional image based on the equal-area projection. The equal-area projection is a projection in which a ratio (area scale) between the area on the earth and the corresponding area on the map is the same. As the equal-area projection, various projections such as the Mollweide projection, the Sinusoidal projection, and the Lambert equal-area projection can be used, and an example using the Goode projection (homolosine projection) will be described hereinafter.

Figure 2:
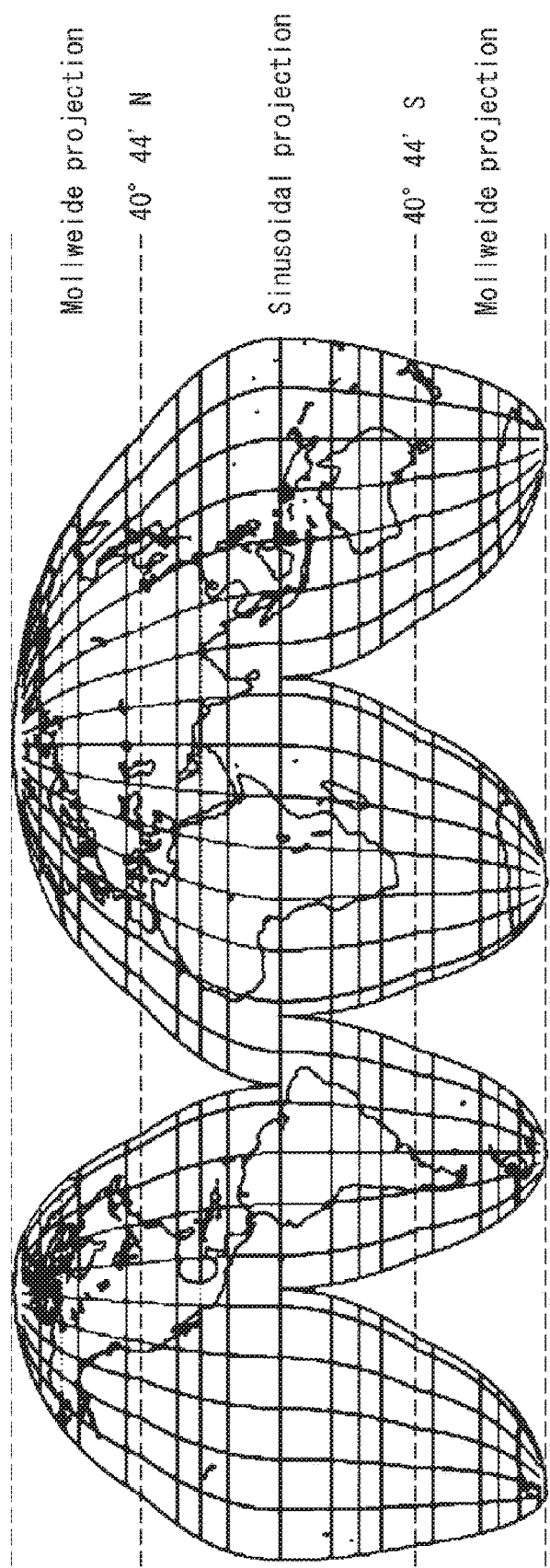
FIG. 2 is a view for describing generation of a developed image performed by a control unit illustrated in FIG. 1.

As illustrated in FIG. 2, the Goode projection is a projection that divides the earth into a high-latitude area and a low-latitude area, expresses the high-latitude area with the Mollweide projection, expresses the low-latitude area with the Sinusoidal projection, and combines the both. A boundary between the high-latitude area and the low-latitude area is a predetermined latitude of 40° 44' with the same parallel length when the area scale is the same in the Mollweide projection and the Sinusoidal projection. Since the Mollweide projection and the Sinusoidal projection are equal-area projections, the Goode projection is also an equal-area projection.

Figure 3:
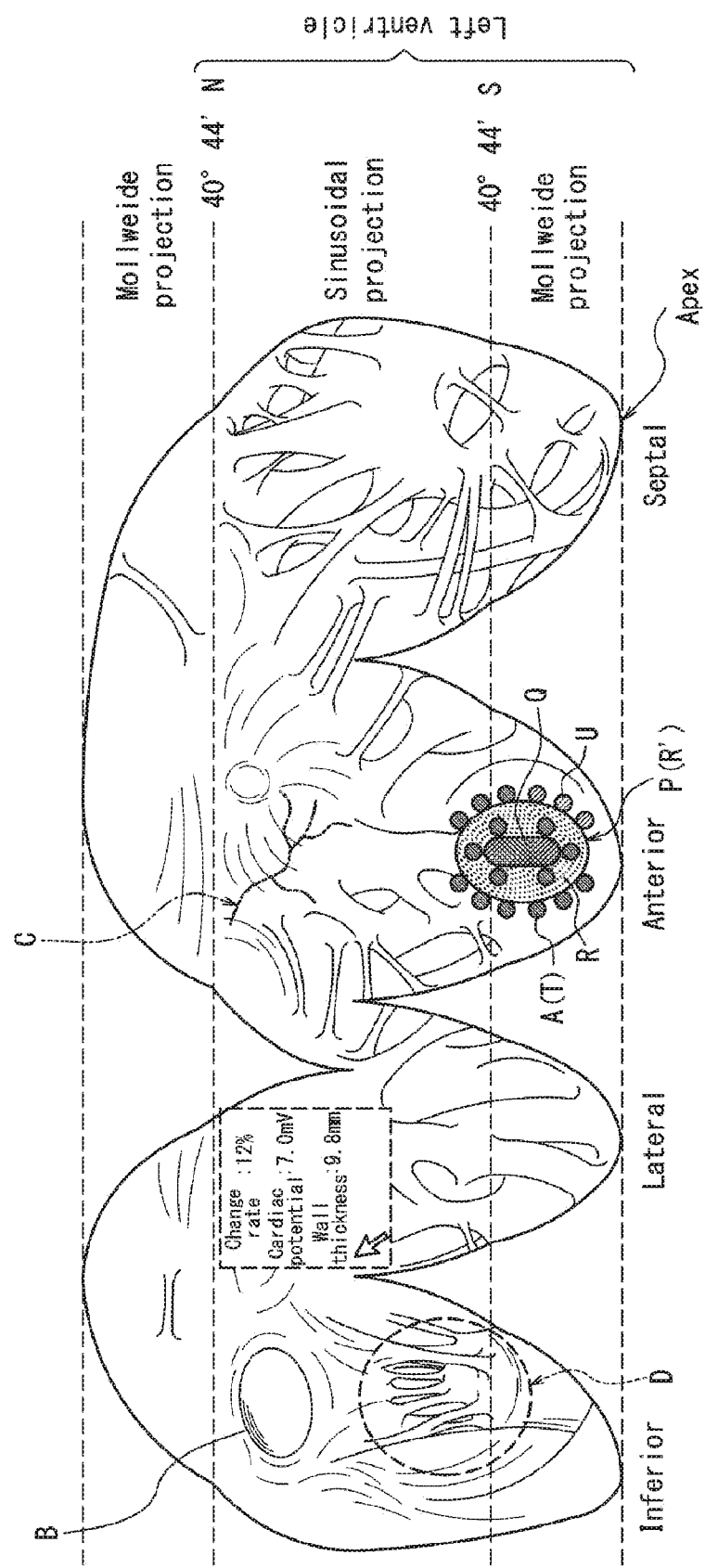
FIG. 3 is a view illustrating an example of a developed image generated by the control unit illustrated in FIG. 1.

For example, when generating a developed image of an inner wall of a left ventricle of a heart, the control unit 16 uses the entire inner wall of the left ventricle as the ground surface of the earth, and generates a two-dimensional image by mapping three-dimensional position data of the inner wall of the left ventricle to two-dimensional position data based on the Goode projection. Specifically, for example, the control unit 16 associates a cardiac apex of the heart with the south pole of the earth, and develops the inner wall of the left ventricle in an area corresponding to 40° 44'N from the south pole based on the Goode projection as illustrated in FIG. 3. Here, the control unit 16 associates four areas each having the cardiac apex corresponding to the south pole as a lower end with a front wall, a rear wall (lower rear wall), a left wall (side wall), a right wall (septum) the left ventricle, respectively. In FIG. 3, the rear wall, the left wall, the front wall, and the right wall are associated in this order from the left area. In this manner, the control unit 16 develops the inner wall of the atrium and ventricle (the left ventricle in the example of FIG. 3) of the heart indicated in the three-dimensional structure information into the two-dimensional image based on the Goode projection, which is the equal-area projection, and generates the developed image interrupted by dividing the two-dimensional image into the front wall, the rear wall, the left wall, and the right wall of the atrium and ventricle.

Since the inner wall of the atrium and ventricle of the heart is developed into the two-dimensional image based on the equal-area projection, it is possible to accurately grasp sizes of a region of interest (such as an infarct region) and a treatment region (such as an injection region of a material to be administered), a proportion in the inner wall, and the like. In addition, since the development is performed to be divided (interrupted) into the front wall, the rear wall, the left wall, and the right wall of the atrium and ventricle of the heart, it is possible to intuitively grasp the relationship between each part on the developed image after the interruption and each of the front wall, rear wall, left wall, and right wall of the atrium and ventricle. As a result, it is possible to intuitively and more accurately grasp positions of the region of interest and the treatment region in the atrium and ventricle.

In addition, the control unit 16 may make a mode (for example, a color) of a region of interest different from a mode of the other regions on a developed image in the present embodiment. For example, the control unit 16 can set a color of the infarct region, which is the region of interest, to a color complementary to a color of a normal region which is the other region. In this manner, the region of interest can be easily grasped while being distinguished from the other region. The region of interest is not limited to the above-described infarcted region, and includes a hibernating myocardium whose motion amount has decreased due to chronic ischemia, a stunned myocardium whose motion amount has decreased due to acute ischemia, and the like. The control unit 16 may express only one of these in a different mode from other regions as the region of interest, or may express all of them in a different mode from other regions as the regions of interest. Incidentally, the region of interest may be identified by the control unit 16 based on the three-dimensional structure information, or may be identified by, for example, a treatment worker based on the three-dimensional structure information. In FIG. 3, an infarcted region Q and a target region R, which corresponds to a hibernating myocardium and a stunned myocardium and is a treatment target region, are used as the regions of interest. The target region R is a region obtained by excluding the infarct region Q from the low-motion region P which is an abnormal region R'. Furthermore, FIG. 3 illustrates a target injection point U, which is a target position to inject a material to be administered, and a marker A indicating an injection point T which is a position to which the material to be administered has been actually injected and is the treatment region. Details of the identification of the region of interest performed by the control unit 16 will be described later.

In addition, the control unit 16 may identify a position of a heart valve based on the three-dimensional structure information and map the identified heart valve to a corresponding position on the developed image. Since the heart valve that controls the entry and exit of blood into the atrium and ventricle is mapped to the corresponding position on the developed image, it is possible to intuitively and more accurately grasp the region of interest and the treatment region. In addition, since the heart valve is mapped to the corresponding position on the developed image, an anatomical positional relationship can be accurately grasped in either a cardiac dilated disease (dilated cardiomyopathy) or a cardiac hypertrophic disease (hypertrophic cardiomyopathy). For example, when generating the developed image of the inner wall of the left ventricle of the heart, it is preferable that the control unit 16 map at least one of an aortic valve and a mitral valve to a corresponding position on the developed image as a heart valve B as illustrated in FIG. 3. In addition, the control unit 16 may display an open/closed state of the heart valve on the developed image. Since the open/closed state of the heart valve is displayed on the developed image, it is possible to accurately grasp whether the heart is in the diastole or the systole, or each timing of the diastole and the systole of the heart.

In addition, the control unit 16 may map a three-dimensional structure in the atrium and ventricle of the heart indicated in the three-dimensional structure information on the developed image by a projection of expressing the three-dimensional structure with saturation and lightness. In this manner, the inner surface of the atria and ventricle can be displayed in a three-dimensional manner in a developed image as illustrated in FIG. 3. There is a papillary muscle (e.g., trabeculae carneae) extending in a streak shape in the ventricle of the heart, and the interior of the ventricle has a complex three-dimensional structure (irregular structure). For example, the control unit 16 may map the three-dimensional structure such as a papillary muscle D on the developed image as illustrated in FIG. 3. In this manner, it is possible to more intuitively and accurately grasp the state of the inner wall of the atrium and ventricle of heart. In addition, the control unit 16 may be also configured so as not to map a specific irregular structure, for example, the irregular structure corresponding to the papillary muscle, on the developed image. That is, the control unit 16, which is the image generation unit, can switch the presence/absence of mapping of the three-dimensional structure corresponding to the papillary muscle on the developed image. In addition, the control unit 16 may or does not necessarily map an irregular structure corresponding to a chorda tendinea on the developed image. That is, the control unit 16, which is the image generation unit, may be configured to be capable of switching the presence/absence of mapping of the three-dimensional structure corresponding to the chorda tendinea on the developed image.

As a projection of expressing the three-dimensional structure with saturation and lightness, a projection of creating a red three-dimensional map that expresses a three-dimensional structure of a ground surface with saturation and lightness can be used. In this projection, the degree of swell and sink in a local area (for example, the degree of a ridge valley of a topographic map) is displayed in a corresponding area on a two-dimensional surface with gradations relating to lightness. In addition, in this projection, a gradient distribution of a plane connecting a coordinate point sequence that maps a vector field (a set of topographic data representing the ground surface) to a three-dimensional coordinate space is displayed with a color tone relating to saturation (preferably a reddish color). With such a projection, it is possible to obtain an image that has no direction dependency and enables observation of terrains (three-dimensional structure) in all directions at the same time. Incidentally, the above-described projection is described in, for example, Japanese Patent No. 3670274 and the detailed description thereof is omitted herein.

In addition, the information input unit 11 may receive as an input time-series three-dimensional structure information including the diastole and the systole of the heart. In this case, the control unit 16 may generate a developed image during the diastole and a developed image during the systole, and correct a position of the infarct region Q (see FIG. 3), which is a part of the region of interest, for example, based on these developed images. The position of the infarct region Q does not change greatly during the diastole nor systole of the heart. Therefore, for example, when there is an area where the position changes greatly between the developed image during the diastole and the developed image during the systole, the control unit 16 may correct the region of interest by excluding the area from the region of interest since there is a high possibility that the area is not the infarct region Q. In this manner, the position of the region of interest can be identified more accurately.

In addition, the control unit 16 may obtain a wall thickness of the inner wall facing the atria and ventricles of the heart based on the three-dimensional structure information. However, the information input unit 11 may receive as an input scale information such as heart wall thickness information acquired by a device such as a computed tomography device, a magnetic resonance imaging device, and a three-dimension ultrasonography device, together with another three-dimensional structure information of the heart. When the control unit 16 obtains the wall thickness of the inner wall facing the atria and ventricles of the heart, for example, it is possible to use body shape information, such as a chest circumference of a subject, measured in advance and acquired through the information input unit 11 or the operation input unit 13, for example. For example, the control unit 16 may calculate an average value, a minimum value, or a maximum value of the wall thickness in a predetermined area for each predetermined area of the inner wall facing the atria and ventricles of the heart. In addition, the control unit 16 may calculate the wall thickness only at a plurality of locations on the inner wall facing the atria and ventricles of the heart, for example. The plurality of locations on the inner wall facing the atria and ventricles of the heart may be, for example, a plurality of locations set at equal intervals in the circumferential direction along an outline of the heart in a cross-sectional image obtained by cutting the heart. In other words, the wall thickness may be calculated at the plurality of locations set such that a central angle becomes a predetermined angle in one cross-sectional image of the heart.

The control unit 16 may map the calculated or acquired wall thickness of the inner wall facing the atria and ventricles of the heart on the developed image. That is, the control unit 16 may express the wall thickness obtained for each position of the inner wall at a corresponding position on the developed image using gradations or the like depending on the wall thickness. In addition, the control unit 16 may display the generated developed image on the display unit 14, and may display a wall thickness at a position (for example, pop-up display) together with an arrow indicating a position given in instruction as illustrated in FIG. 3 when the operation input unit 13 receives an operation input giving an instruction on the position on the displayed developed image. The control unit 16 may display, for example, at least one of an average value, a minimum value, and a maximum value of the wall thickness as wall thickness information in a predetermined area for each predetermined area of the inner wall facing the atria and ventricles of the heart. In addition, the control unit 16 may display the wall thickness only at a plurality of locations on the inner wall facing the atria and ventricles of the heart, for example.

In this manner, the wall thickness of the inner wall is mapped on the developed image, and thus, it is possible to grasp, in advance, a depth to which a material to be administered needs to be injected, for example, when the material to be administered is injected from the inner wall into the myocardium. In addition, it is possible to prevent a needle-shaped injection member used at the time of injecting the material to be administered from penetrating the heart wall.

In addition, the information input unit 11 may acquire electrocardiogram information indicating the electrocardiogram of the inner wall of the heart. Such electrocardiogram information can be acquired, for example, by bringing a catheter having an electrode at a distal end into contact with the inner wall of the heart. The control unit 16 may map the electrocardiogram of each part of the inner wall of the heart indicated by the electrocardiogram information acquired by the information input unit 11 on the developed image. For example, the control unit 16 may express the electrocardiogram of each part of the inner wall, indicated by the electrocardiogram information, at a corresponding position on the developed image using gradations depending on the electrocardiogram. In addition, when the operation input unit 13 receives an operation input giving an instruction on a position on the developed image displayed on the display unit 14, the control unit 16 may display the electrocardiogram at a position (for example, pop-up display) together with an arrow indicating a position given in instruction as illustrated in FIG. 3.

In one embodiment, it may be known that the electrocardiogram is less than 7.0 mV at the infarct region, and the electrocardiogram is 7.0 mV or more at the normal region. Therefore, mapping may be performed by expressing, for example, a position on the inner wall of the heart where the electrocardiogram is less than a predetermined threshold (for example, less than 7.0 mV) with a different color from other positions. Since the electrocardiogram of the inner wall is mapped on the developed image, it becomes easy to grasp the infarct region Q (see FIG. 3) on the inner wall of the heart.

In addition, the control unit 16 may obtain a wall motion state (a displacement amount, a displacement direction, a displacement speed, and the like) of the inner wall of the atria and ventricles of the heart based on the time-series three-dimensional structure information. For example, the control unit 16 sets a straight line extending from a center point C of the heart toward the outside of the heart, sets a point where the straight line intersects the inner wall as a point N(t), sets a point where the straight line intersects the inner wall whose position has changed after a lapse of a few seconds as a point N(t+1), and subtracts a distance (line segment CN(t+1)) from the center point C to the point N(t+1) from a distance (line segment CN(t)) from the center point C to the point N(t) to calculate the displacement amount of the inner wall. For example, the control unit 16 may calculate an average value, a minimum value, or a maximum value of the wall motion state in an area for each area of the inner wall facing the atria and ventricles of the heart. In addition, the control unit 16 may calculate the wall motion state only at a plurality of locations on the inner wall facing the atria and ventricles of the heart, for example. The plurality of locations on the inner wall facing the atria and ventricles of the heart may be, for example, a plurality of locations set at equal intervals in the circumferential direction along an outline of the heart in a cross-sectional image obtained by cutting the heart. In other words, the wall motion state may be calculated at the plurality of locations set such that a central angle becomes a predetermined angle in one cross-sectional image of the heart.

The control unit 16 may map the calculated wall motion state of the inner wall of the atria and ventricles of the heart on the developed image. For example, when the operation input unit 13 receives an operation input giving an instruction on a position on the developed image displayed on the display unit 14, the control unit 16 may display the wall motion state at a position (for example, pop-up display) together with an arrow indicating a position given in instruction as illustrated in FIG. 3. FIG. 3 illustrates an example in which a change rate of a distance between two points of the heart during the diastole and systole of the heart is illustrated as the wall motion state. It may be known that wall motion decreases in an abnormal region (such as an infarct region, a hibernating myocardium whose motion amount has decreased due to chronic ischemia, and a stunned myocardium whose motion amount has decreased due to acute ischemia) as compared with a normal myocardium. Therefore, it becomes easy to grasp the abnormal region on the inner wall of the heart by mapping the wall motion state of the inner wall on the developed image. Incidentally, an example of a specific method for determining a low-motion region where wall motion is decreasing will be described later (see FIGS. 7A to 7C).

In addition, the control unit 16 may identify a region where the wall motion state of the inner wall and the electrocardiogram of the inner wall satisfy predetermined conditions, and map the identified region on the developed image.

As described above, the wall motion decreases at the abnormal region. Thus, a decrease in wall motion at the infarct region is irreversible. On the other hand, a decrease in wall motion in the stunned myocardium and the hibernating myocardium is reversible. In addition, it may be known that the electrocardiogram is less than 7.0 mV at the infarct region, and the electrocardiogram is 7.0 mV or more at the normal region, the stunned myocardium, and the hibernating myocardium as described above.

There fore, the region where the electrocardiogram and the wallmotion in the inner wall of the heart satisfy the predetermined conditions, that is, the region where the electrocardiogram is the predetermined threshold or more (for example, 7.0 mV or more) and the wall motion is the predetermined threshold or less is the stunned myocardium and the hibernating myocardium. Incidentally, an example of a specific method for determining a low-motion region where wall motion is the predetermined threshold or less will be described later (see FIGS. 7A to 7C).

In addition, the control unit 16 may display the generated developed image on the display unit 14, and may superimpose the marker A indicating the position (the position of the treatment region) given in instruction by the operation input on the developed image as shown in FIG. 3 when the operation input unit 13 receives an operation input giving an instruction on the position of the treatment region on the displayed developed image. In this manner, the treatment region can be displayed on the developed image, and the treatment region on the inner wall of the heart can be accurately stored.

In addition, the control unit 16 may extract a three-dimensional position of a coronary artery located on an outer wall of the heart so as to surround the heart based on the three-dimensional structure information, and develop the position of the coronary artery C two-dimensionally to be mapped on the developed image as illustrated in FIG. 3. Incidentally, the coronary artery C is indicated by a two-dot chain line in FIG. 3. As described above, the developed image is an image obtained by two-dimensionally developing the inner wall of the atria and ventricles of the heart. The control unit 16 maps the coronary artery to the position of the inner wall on the developed image corresponding to the coronary artery as if the coronary artery was seen through the heart wall.

Since the coronary artery is mapped on the developed image, the positional relationship between each location on the developed image and the coronary artery can be grasped intuitively and accurately.

In addition, the control unit 16 may obtain a blood flow rate of the coronary artery based on the three-dimensional structure information, and map the obtained blood flow rate to the coronary artery on the developed image by, for example, texture mapping. The blood flow rate of the coronary artery can be obtained from, for example, a minor-axis cross section of the coronary artery illustrated in the three-dimensional structure information.

In addition, the control unit 16 may generate a developed image at every predetermined timing, for example, based on the time-series three-dimensional structure information, and may sequentially display and store the generated developed image in the time-series order. In addition, the control unit 16 may appropriately combine and display the above-described various types of information (the position of the heart valve, the wall thickness of the inner wall, the electrocardiogram, the wall motion state, the region where the electrocardiogram and the wall motion state satisfy the predetermined conditions, the three-dimensional structure, and the like) on the developed image. In addition, the control unit 16 may switch and display the above-described various types of information as appropriate.

Figure 4:
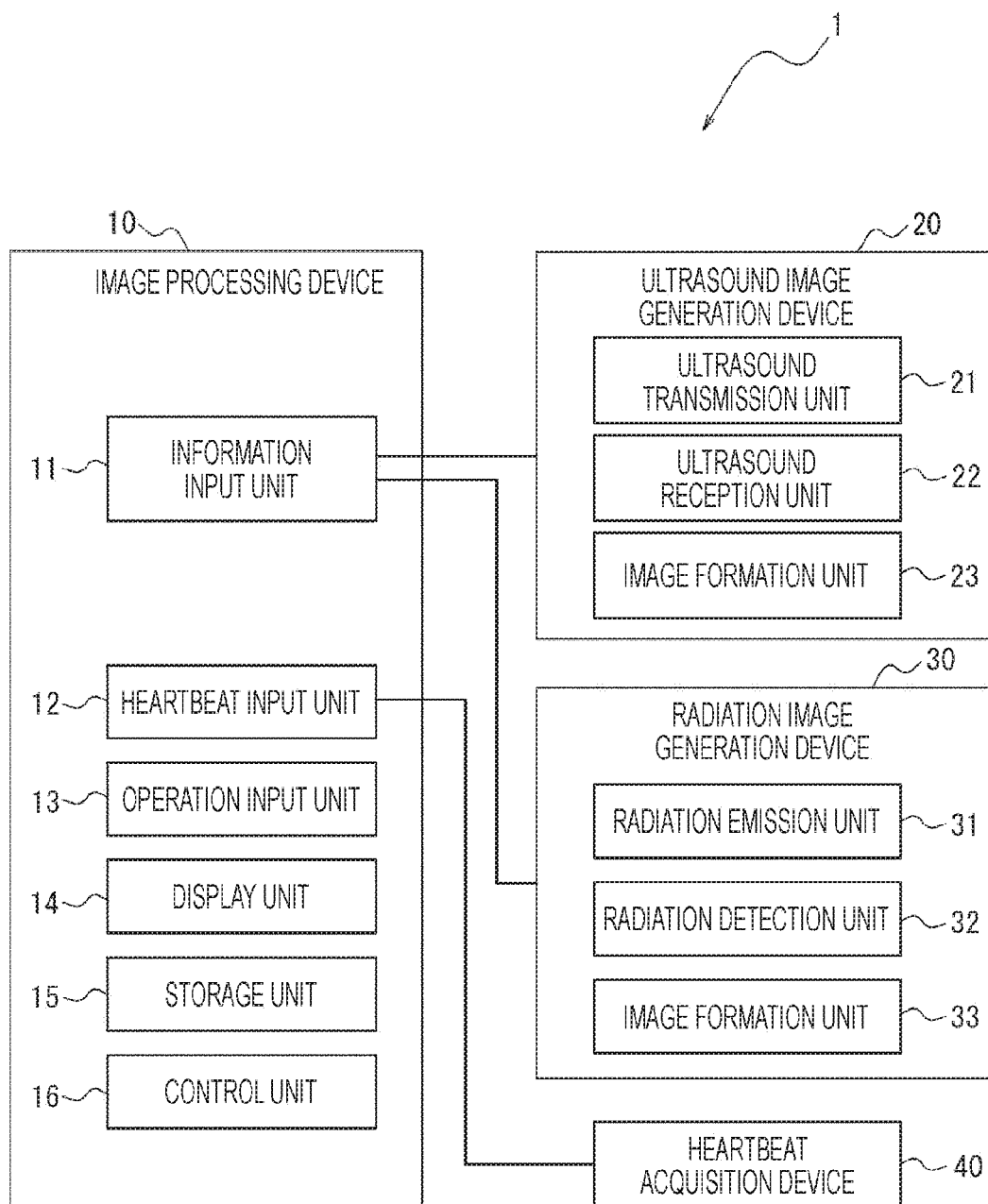
FIG. 4 is a block diagram illustrating a schematic configuration of an image processing system comprising the image processing device illustrated in FIG. 1.

FIG. 4 is a block diagram illustrating a schematic configuration of an image processing system 1 including the image processing device 10 according to the present embodiment. As illustrated in FIG. 4, the image processing system 1 includes the image processing device 10, an ultrasound image generation device 20 serving as a first imaging device, a radiation image generation device 30 serving as a second imaging device, and a heartbeat acquisition device 40. Incidentally, the same components as those in FIG. 1 are denoted by the same reference signs, and the description thereof is omitted in FIG. 4.

The ultrasound image generation device 20 serving as the first imaging device is located outside a subject's body and captures an ultrasound image as a first tomographic image of a heart from outside the subject's body. The ultrasound image generation device 20 includes an ultrasound transmission unit 21 that transmits ultrasound, an ultrasound reception unit 22 that receives the ultrasound, and an image formation unit 23 that forms the first tomographic image based on the ultrasound received by the ultrasound reception unit 22. The ultrasound image generation device 20 transmits the ultrasound from the ultrasound transmission unit 21 toward the heart of the subject and receives the ultrasound reflected from the heart of the subject by the ultrasound reception unit 22 in a state where the ultrasound transmission unit 21 and the ultrasound reception unit 22 are in contact with a body surface of the subject. The ultrasound image generation device 20 processes the ultrasound received by the ultrasound reception unit 22 in the image formation unit 23 to obtain a tomographic image along a traveling plane of the ultrasound as the first tomographic image. The ultrasound image generation device 20 outputs three-dimensional structure information of the heart including the imaged first tomographic image to the information input unit 11 of the image processing device 10.

The ultrasound image generation device 20 may generate a three-dimensional image as the first tomographic image based on a plurality of tomographic images imaged along different planes by changing positions or orientations of the ultrasound transmission unit 21 and the ultrasound reception unit 22. That is, the first tomographic image may be a tomographic image imaged along one plane, or may be a three-dimensional image generated based on a plurality of tomographic images imaged along a plurality of planes.

The radiation image generation device 30 serving as the second imaging device is located outside the subject's body and images a radiation image as a second tomographic image of the heart from outside the subject's body. The radiation image generation device 30 is, for example, a computed tomography device. The radiation image generation device 30 includes a radiation emission unit 31 that emits radiation, a radiation detection unit 32 that detects the radiation, and an image formation unit 33 that forms the second tomographic image based on the radiation detected by the radiation detection unit 32. The radiation image generation device 30 includes the radiation emission unit 31 and the radiation detection unit 32 at positions facing each other around the subject, emits the radiation such as X-rays from the radiation emission unit 31 toward the heart of the subject and detects the radiation that has passed through the heart of the subject by the radiation detector 32 while rotating the radiation emission unit 31 and the radiation detection unit 32 around the subject. The radiation image generation device 30 processes the radiation detected by the radiation detection unit 32 by the image formation unit 33 to obtain a radiation image that is a three-dimensional image of the heart as the second tomographic image. The radiation image generation device 30 outputs three-dimensional structure information of the heart including the imaged second tomographic image to the information input unit 11 of the image processing device 10.

The second imaging device may be a magnetic resonance imaging (MRI) device instead of the radiation image generation device 30. The magnetic resonance imaging device is located outside the subject's body and images a magnetic resonance image as the second tomographic image of the heart from outside the subject's body. The magnetic resonance imaging device includes a magnetic field generation unit that generates a magnetic field, a signal reception unit that receives a nuclear magnetic resonance signal, and an image formation unit that forms a magnetic resonance image, which is a three-dimensional image, as the second tomographic image based on the nuclear magnetic resonance signal received by the signal reception unit.

A contrast agent is administered to the heart of the subject a predetermined time before the second tomographic image is imaged by the radiation image generation device 30 or the magnetic resonance imaging device as the second imaging device. As a result, the second tomographic image imaged by the second imaging device includes a delayed contrast image.

The second imaging device may be a nuclear medicine inspection device that performs a scintigraphy inspection, a single photon emission tomography (SPECT) inspection, a positron emission tomography (PET) inspection, or the like, instead of the radiation image generation device 30 or the magnetic resonance imaging device. The nuclear medicine inspection device is located outside the subject's body and acquires a radioisotope (RI) distribution image as the second tomographic image of the heart from outside the subject's body. The nuclear medicine inspection device obtains the second tomographic image by imaging the distribution of a drug labeled with the radioisotope which has been previously administered to the subject.

The heartbeat acquisition device 40 acquires heartbeat information of the subject. The heartbeat information includes temporal change information of the heartbeat. The heartbeat acquisition device 40 may acquire heartbeat information simultaneously with the imaging of the first tomographic image or the second tomographic image, and associate the heartbeat information with the image. The heartbeat acquisition device 40 is, for example, an electrocardiogram monitor that measures temporal changes in cardiac action potential via electrodes attached to the subject's chest or limbs and continuously displays an electrocardiogram waveform.

As described above, the image processing device 10 is located outside the subject's body and is configured using the information processing device such as the computer. The image processing device 10 illustrated in FIG. 4 further includes a heartbeat input unit 12 in addition to the information input unit 11, the operation input unit 13, the display unit 14, the storage unit 15, and the control unit 16 provided in the image processing device 10 illustrated in FIG. 1.

The information input unit 11 receives inputs of the first tomographic image from the ultrasound image generation device 20 serving as the first imaging device and the second tomographic image from the radiation image generation device 30 serving as the second imaging device, as inputs of the three-dimensional structure information of the heart.

The heartbeat input unit 12 receives as an input the heartbeat information from the heartbeat acquisition device 40. The heartbeat input unit 12 includes an interface that receives information from the heartbeat acquisition device 40 by, for example, wired communication or wireless communication. The heartbeat input unit 12 outputs the input heartbeat information to the control unit 16.

Under the control of the control unit 16, the display unit 14 displays the developed image of the inner wall of the heart generated by the control unit 16 based on the three-dimensional structure information of the heart such as the first tomographic image and the second tomographic image.

The storage unit 15 stores various types of information and programs configured to cause the control unit 16 to execute a specific function. The storage unit 15 stores, for example, the three-dimensional image of the heart as the three-dimensional structure information of the heart. The three-dimensional image of the heart is the first tomographic image and the second tomographic image. In addition, the storage unit 15 stores the developed image of the heart generated by the control unit 16. The developed image of the heart includes the infarct region Q and the target region R as the regions of interest. As described above, the target region R (see FIG. 7C) of the heart as a part of the region of interest of the heart is the region obtained by excluding the infarct region Q (see FIG. 7B) from the low-motion region P (see FIG. 7A), which is the abnormal region R', and is the hibernating myocardium whose motion amount has decreased due to chronic ischemia and the stunned myocardium whose motion amount has decreased due to acute ischemia. However, the region of interest is not limited to the infarct region Q and the target region R, and can be set as appropriate. For example, only the infarct region Q (see FIG. 7B) or only the target region R may be set as the region of interest. For example, the storage unit 15 stores a plurality of developed images based on a plurality of tomographic images imaged at different times. The storage unit 15 stores, for example, the dose and physical property information of the material to be administered which is to be injected into the abnormal region R' by a treatment using the injection member to be described later. The storage unit 15 stores, for example, shape information of the injection member.

The control unit 16 controls an operation of each component that constitutes the image processing device 10. The control unit 16 executes a specific function by reading a specific program. For example, the control unit 16 generates the developed image based on the three-dimensional structure information of the heart such as the first tomographic image and the second tomographic image. The three-dimensional structure information of the heart used when the control unit 16 generates the developed image is not limited to the first tomographic image and the second tomographic image described above, and the control unit 16 can also generate the developed image using another three-dimensional structure information of the heart. The control unit 16 causes the display unit 14 to display the generated developed image. The control unit 16 may output the generated developed image to an external display device. The control unit 16 includes a processor, for example.

The control unit 16 may correct the first tomographic image based on the second tomographic image when the second tomographic image is imaged by the radiation image generation device 30 or the magnetic resonance imaging device. For example, the control unit 16 can correct the first tomographic image based on the second tomographic image by detecting each of a feature point in the first tomographic image and a feature point in the second tomographic image by pattern recognition or the like and replacing an area including the feature point in the first tomographic image with an area in the second tomographic image including the corresponding feature point. As a result, the first tomographic image can be corrected with a higher-definition second tomographic image, and thus, the information on the structure and shape of the heart can be illustrated more accurately.

Figure 5:
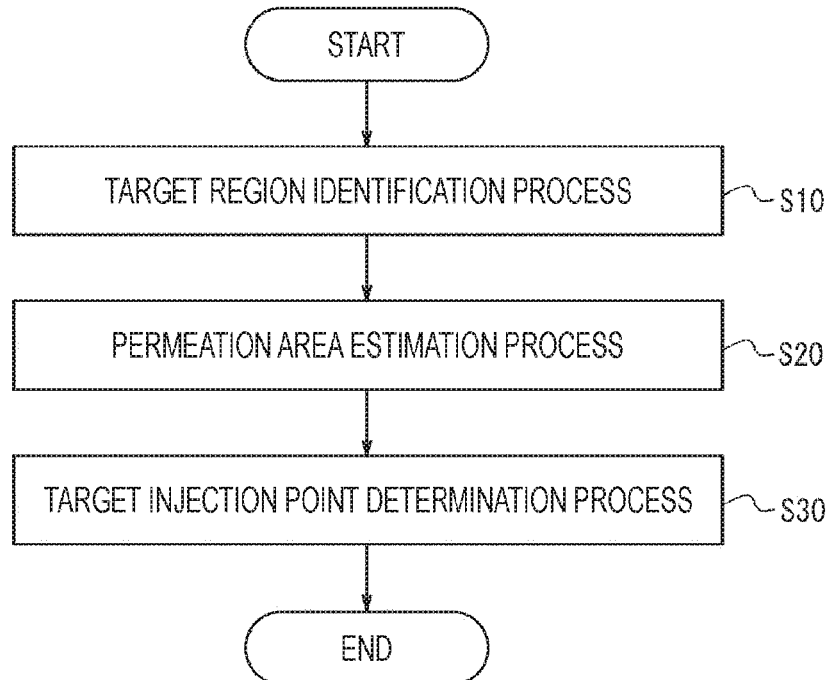
FIG. 5 is a flowchart illustrating an example of an operation of the image processing device illustrated in FIG. 4.

FIG. 5 is a flowchart illustrating an example of an operation of the image processing device 10. Incidentally, hereinafter, a description will be given regarding an example in which the image processing device 10 performs a process of identifying the target region R (see FIG. 7C) based on the first tomographic image and the second tomographic image as the three-dimensional structure information of the heart. In addition, hereinafter, a description will be given regarding an example in which a process of estimating a permeation area where the material to be administered permeates and a process of determining a target injection point to inject the material to be administered are performed when the image processing device 10 injects the material to be administered into a predetermined position on the inner wall of the heart. However, it is not essential for the image processing device 10 to perform these processes in the present embodiment. The identification of the target region, the estimation of the permeation area, the determination of the target injection point, and the like may be performed in advance by a medical worker or the like based on the three-dimensional structure information of the heart obtained in advance.

As illustrated in FIG. 5, the image processing device 10 first performs a target region identification process of identifying the target region R (step S10). Next, when a material to be administered is injected into a predetermined position on the inner wall of the heart, the image processing device 10 performs a permeation area estimation process of estimating a permeation area where the material to be administered permeates (step S20). Finally, the image processing device 10 performs a target injection point determination process of determining a target injection point to inject the material to be administered (step S30).

Figure 6:
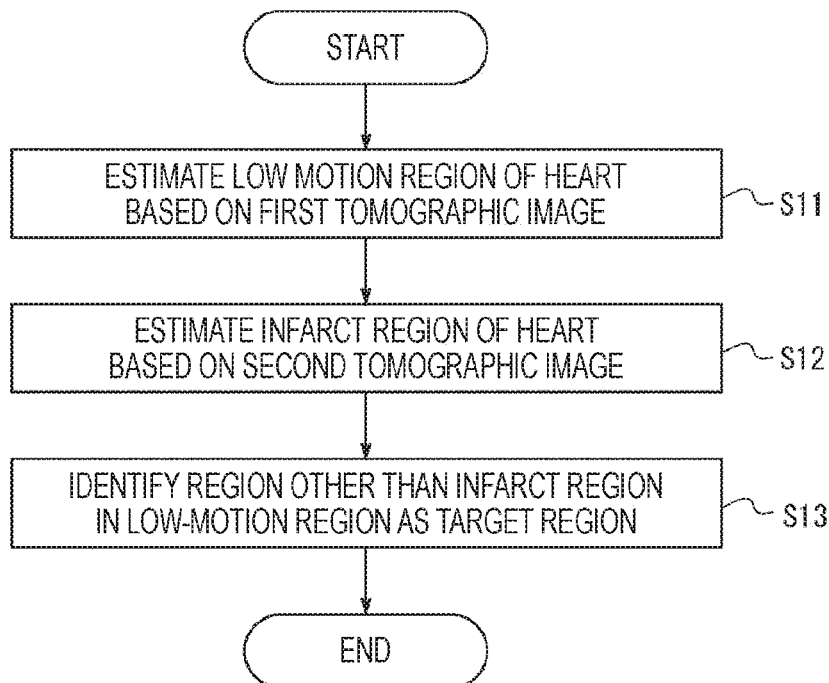
FIG. 6 is a flowchart illustrating details of a target region identification process performed by the image processing device illustrated in FIG. 4.
Figure 7A:
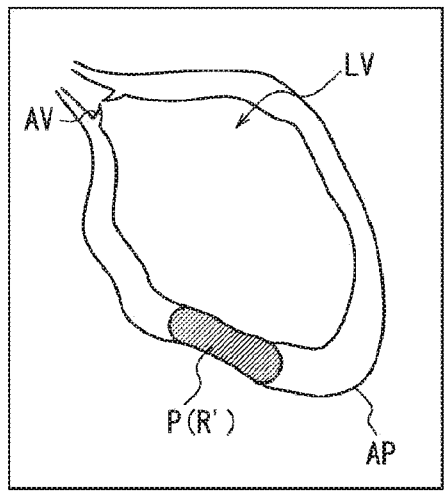
FIG. 7A is a view for describing a target region identification process performed by the image processing device illustrated in FIG. 4.
Figure 7B:
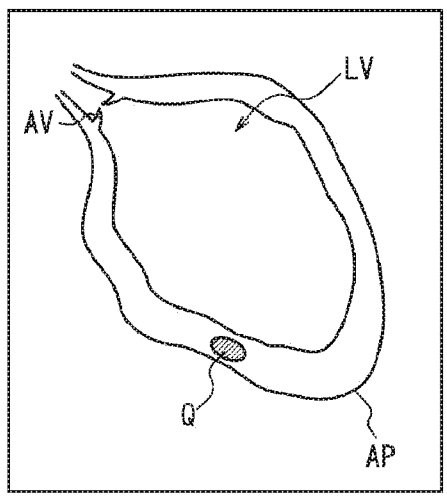
FIG. 7B is a view for describing the target region identification process performed by the image processing device illustrated in FIG. 4.
Figure 7C:
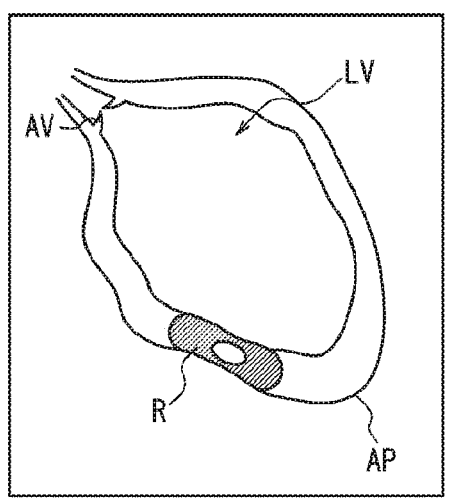
FIG. 7C is a view for describing the target region identification process performed by the image processing device illustrated in FIG. 4.

FIG. 6 is a flowchart illustrating details of the target region identification process performed by the image processing device 10. FIGS. 7A to 7C are views for describing the target region identification process performed by the image processing device 10 and are views illustrating cross sections of a left ventricle LV of the heart. As illustrated in FIG. 7A, the control unit 16 reads the first tomographic image input via the information input unit 11, and estimates the low-motion region P of the heart based on the first tomographic image (step S11: a low-motion region estimation step). Specifically, the information input unit 11 receives inputs of a plurality of the first tomographic images imaged at predetermined time intervals. Then, the control unit 16 estimates the low-motion region P based on temporal changes of the plurality of first tomographic images. More specifically, the control unit 16 first extracts, as feature points, a plurality of points whose luminance is a predetermined value or more out of the first tomographic image. The control unit 16 extracts the plurality of feature points from the plurality of first tomographic images imaged at different times including the diastole in which the myocardium is most dilated and the systole in which the myocardium is most deflated. The control unit 16 calculates a change rate obtained by measuring a distance between an arbitrary feature point and another adjacent feature point between the first tomographic image during the diastole and the first tomographic image during the systole. The control unit 16 estimates that a region of the heart corresponding to an area where the change rate is a predetermined threshold or lower is the low-motion region P. The predetermined threshold of the change rate is, for example, 12%, but may be appropriately changed depending on the setting.

As illustrated in FIG. 7B, the control unit 16 reads the second tomographic image input via the information input unit 11, and estimates the infarct region Q of the heart based on the second tomographic image (step S12: an infarct region estimation step). The infarct region Q is a region where the myocardium is turned into an ischemic state and becomes necrosis. The infarct region Q has the above change rate equal to or lower than the predetermined threshold and is included in the low-motion region P. Specifically, when the second tomographic image includes a delayed contrast image, the control unit 16 estimates the infarct region Q based on the delayed contrast image of the second tomographic image. Specifically, the control unit 16 estimates that a region where the delayed contrast image has been reflected is the infarct region Q. When the second tomographic image is a radioisotope distribution image, the control unit 16 estimates the infarct region Q based on the radioisotope distribution. Specifically, the control unit 16 estimates that the accumulation defect site where radioisotopes are not accumulated is the infarct region Q. The control unit 16 may execute the infarct region estimation step (step S12) prior to the above-described low-motion region estimation step (step S11).

As illustrated in FIG. 7C, the control unit 16 identifies a region other than the infarct region Q estimated in the infarct region estimation step (step S12) in the low-motion region P estimated in the low-motion region estimation step (step S11) as the target region R (step S13: a target region identification process). The target region R is a region where the above-described change rate is equal to or lower than the predetermined threshold but is not necrotic, and is the hibernating myocardium and the stunned myocardium. The control unit 16 maps the identified target region R on the developed image as a part of the region of interest. Incidentally, the control unit 16 maps the infarct region Q as a part of the region of interest on the developed image in addition to the target region R (see FIG. 3). Incidentally, the low-motion region P, which is the abnormal region R', may be mapped on the developed image without distinguishing the infarct region Q and the target region R as the region of interest. The target region R includes the hibernating myocardium and the stunned myocardium, but the both exist independently of each other. The hibernating myocardium is a chronic ischemic state. The stunned myocardium is an acute ischemic state. The stunned myocardium is caused by overload due to resumption of blood flow. Therefore, the region of the stunned myocardium can be identified by causing an overload state and eliminating the state. As a result, the stunned myocardium and the hibernating myocardium can be selected.

The heart repeats contraction and expansion accompanying the heartbeats. Therefore, it is preferable that an expansion/contraction state of the heart in the first tomographic image used in the low-motion region estimation step (step S11), and an expansion/contraction state of the heart in the second tomographic image used in the infarct region estimation step (step S12) be states which are the same or approximate. Therefore, the control unit 16 selects a first tomographic image corresponding to the expansion/contraction state of the heart in the second tomographic image from the plurality of first tomographic images, and uses the selected first tomographic image to identify the target region R. The expansion/contraction state of the heart in the first tomographic image may be estimated based on position information of the feature point by detecting the feature point from the first tomographic image by pattern recognition or the like. Similarly, the expansion/contraction state of the heart in the second tomographic image may be estimated based on position information of the feature point by detecting the feature point from the second tomographic image by pattern recognition or the like. Examples of the feature point include a cardiac apex AP or an aortic valve AV. The expansion/contraction state of the heart in the first tomographic image and the second tomographic image may be determined based on the heartbeat information input via the heartbeat input unit 12. Specifically, the first tomographic image and the second tomographic image are associated with pieces of heartbeat information of the heart at the time of imaging, and the expansion/contraction state of the heart in the first tomographic image and the second tomographic image is determined by the associated pieces of heartbeat information.

As described above, the image processing device 10 can identify the hibernating myocardium and the stunned myocardium having a relatively high treatment effect as the target region R, which can contribute to the improvement of the treatment effect.

Figure 8:
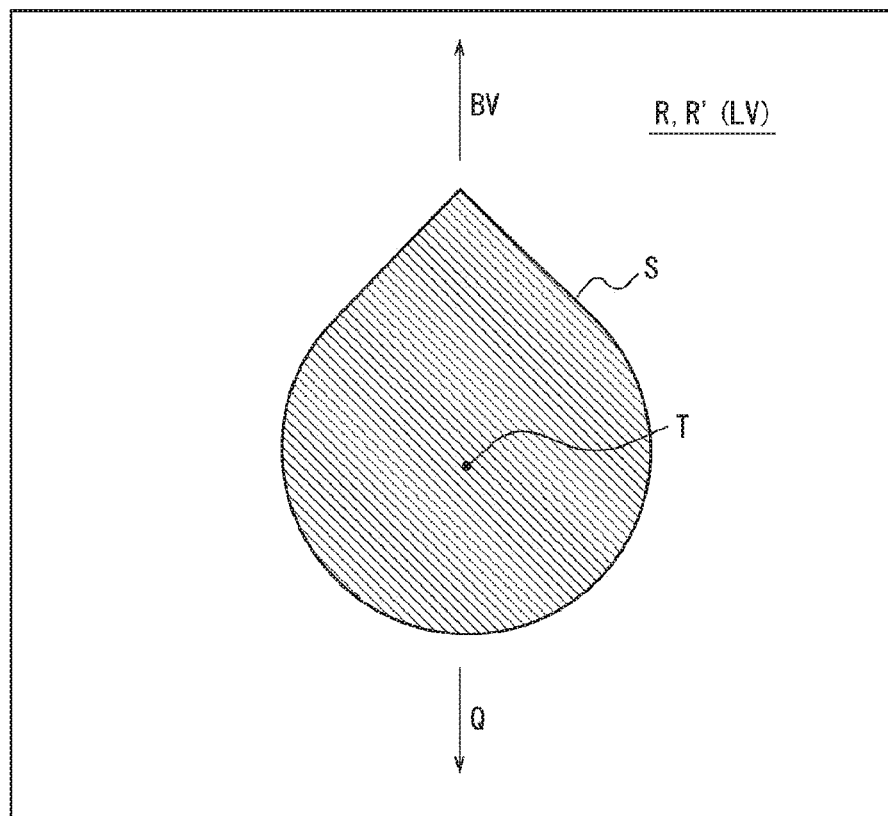
FIG. 8 is a schematic view illustrating an example of a permeation area S estimated by a permeation area estimation process performed by the image processing device illustrated in FIG. 4.

FIG. 8 is a schematic view illustrating an example of a permeation area S estimated by the permeation area estimation process performed by the image processing device 10. FIG. 8 is a view illustrating a heart wall cross section of the left ventricle LV of the heart and illustrates a range of the permeation area S located in the abnormal region R'. When assuming that the material to be administered is injected at an arbitrary injection point T of the abnormal region R' included in the developed image of the heart, the control unit 16 estimates the permeation area S where the administration subject permeates (a permeation area estimation step). The control unit 16 may superimpose the estimated permeation area S on the developed image. The permeation area S of the present embodiment is included in the target region R (see FIG. 7C) identified by the above-described target region identification process out of the abnormal region R' (see FIG. 7A) of the heart. The material to be administered is, for example, a biological substance such as a cell or a substance such as a biomaterial. The permeation area S is a region after a lapse of a predetermined time within a time period during which an effect of the material to be administered is obtained since the injection of the material to be administered.

For example, the control unit 16 estimates a position of the blood vessel BV in the heart based on the three-dimensional image, and estimates the permeation area S based on the position of the injection point T relative to the position of the blood vessel BV. It is considered that the material to be administered that is injected into the target region R is likely to permeate in a direction of the blood vessel BV near the blood vessel BV due to the influence of blood flow. Therefore, the control unit 16 estimates that the permeation area S extends in the direction of the blood vessel BV as the injection point T is closer to the blood vessel BV as illustrated in FIG. 8. For example, the control unit 16 estimates the position of the infarct region Q (see FIG. 7B) based on the three-dimensional structure information, and estimates the permeation area S based on the position of the injection point T relative to the position of the infarct region Q. It is considered that the material to be administered which is injected into the target region R is less likely to permeate in a direction of the infarct region Q because the heart activity such as blood flow and heartbeat decreases near the infarct region Q. Therefore, the control unit 16 estimates that the extension of the permeation area S in the direction of the infarct region Q is hindered as the injection point T is closer to the infarct region Q as illustrated in FIG. 8.

The control unit 16 may estimate the permeation area S based on the dose and physical property information of the material to be administered stored in the storage unit 15. Specifically, the control unit 16 estimates that the permeation area S increases as the dose of the material to be administered increases. The control unit 16 may estimate the permeation area S based on the wall thickness of the heart wall calculated by the control unit 16 or the wall thickness of the heart wall acquired from a device such as a computed tomography device. Specifically, the control unit 16 estimates that the permeation area S becomes wider along the heart wall as the wall thickness near the injection point T is thinner. The control unit 16 may estimate the permeation area S based on temporal changes of a plurality of three-dimensional images stored in the storage unit 15. Specifically, the control unit 16 detects temporal changes of a position of a feature point in the plurality of three-dimensional images, and estimates a motion caused by heartbeats or the like for each region of the heart wall based on the temporal changes of the position of the feature point. Then, it is estimated that the permeation area S is larger as the region actively moves. Conversely, it is estimated that the permeation area S is smaller in the infarct region Q that hardly moves. The control unit 16 may estimate the permeation area S based on the shape information of the injection member stored in the storage unit 15. The injection member is configured using, for example, a needle-like member, and a side hole configured to discharge the material to be administered is formed around the injection member. Examples of the shape information of the injection member include an outer shape (a linear shape, a curved shape, a spiral shape, and the like), a diameter size, a side hole position, a side hole size, and the like of the injection member.

As described above, the image processing device 10 can estimate the permeation area S where the material to be administered, which has been injected at the arbitrary injection point T of the abnormal region R' permeates in advance, and thus, a treatment simulation can be performed before performing the treatment.

Figure 9:
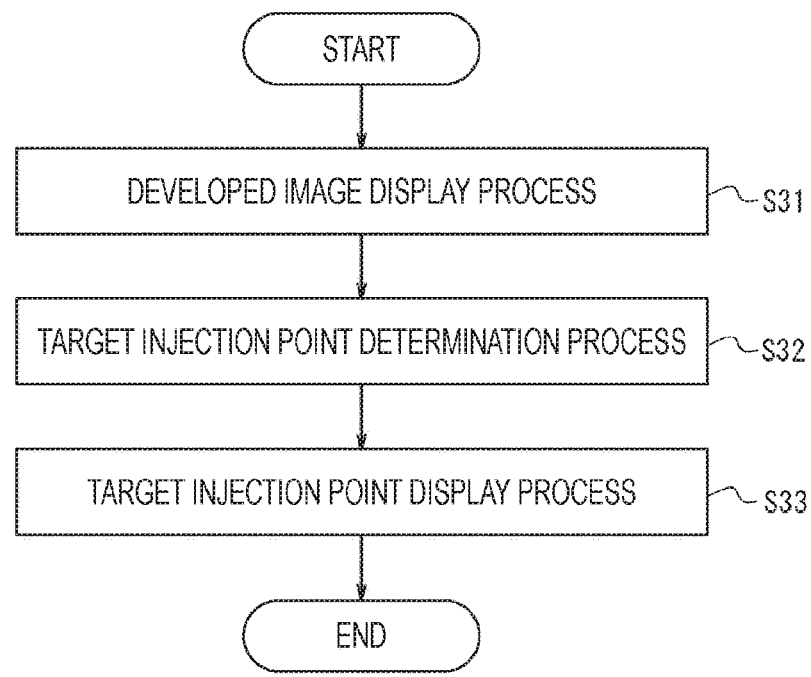
FIG. 9 is a flowchart illustrating details of a target injection point determination process performed by the image processing device illustrated in FIG. 4.
Figure 10A:
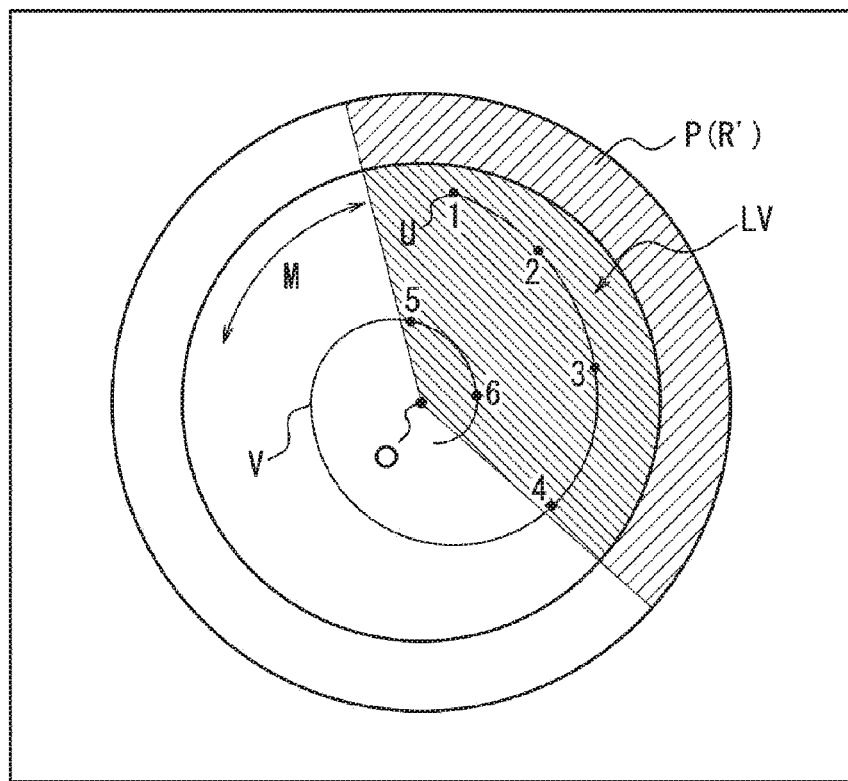
FIG. 10A is a schematic view illustrating an example of a target injection point determined by the target injection point determination process performed by the image processing device illustrated in FIG. 4.
Figure 10B:
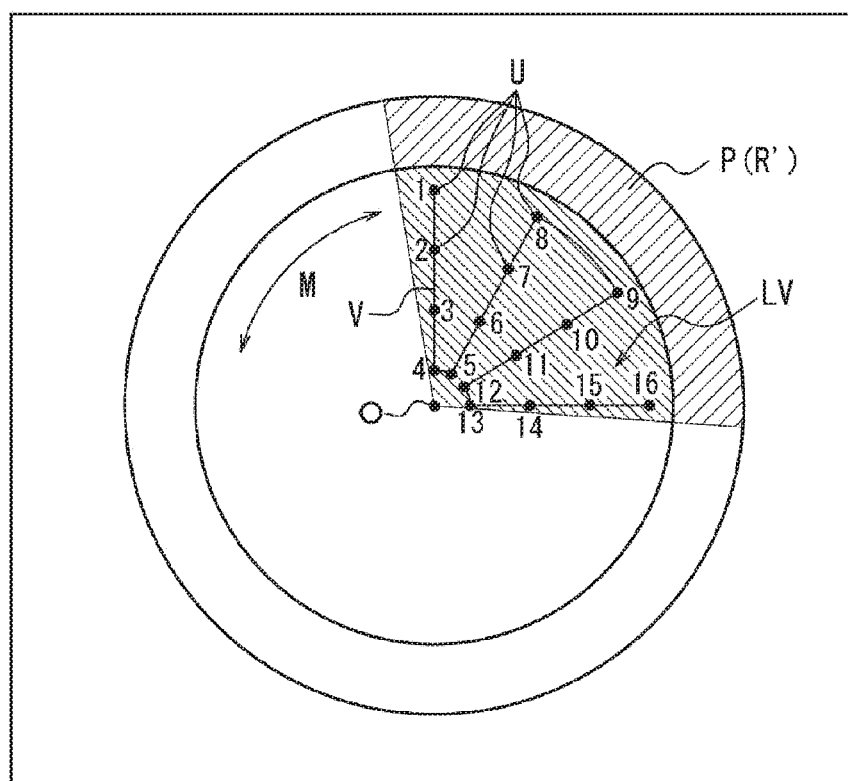
FIG. 10B is a schematic view illustrating an example of the target injection point determined by the target injection point determination process performed by the image processing device illustrated in FIG. 4.

FIG. 9 is a flowchart illustrating details of the target injection point determination process performed by the image processing device 10. FIGS. 10A and 10B are schematic views illustrating examples of the target injection point U determined by the target injection point determination process performed by the image processing device 10. FIGS. 10A and 10B are cross-sectional views of the left ventricle LV of the heart as viewed from the aortic valve AV (see FIGS. 7A to 7C) to the cardiac apex AP (see FIGS. 7A to 7C). The control unit 16 reads the developed image stored in the storage unit 15 and displays the developed image on the display unit 14 (step S31: a developed image display step). The control unit 16 determines positions of a plurality of target injection points U through which the material to be administered needs to be injected to the abnormal region R' based on the three-dimensional structure information of the heart (step S32: a target injection point determination step). The control unit 16 causes the display unit 14 to display the determined plurality of target injection points U to be superimposed on the developed image (step S33: a target injection point display step). The position of the target injection point U includes information on a depth along the wall thickness direction from an inner surface of the heart wall. In other words, the target injection point U indicates at which position from the inner surface of the heart wall and how deep the material to be administered needs to be injected. The position of the target injection point U is determined based on, for example, the permeation area S estimated by the above-described permeation area estimation process. Specifically, the control unit 16 estimates the permeation areas S for the plurality of injection points T, respectively, and determines the injection point T at which the material to be administered needs to be injected as the target injection point U based on the estimated plurality of permeation areas S. For example, the control unit 16 identifies the injection point T corresponding to the permeation area S enclosed by the other plurality of permeation areas S. Then, an injection point T other than the identified injection point T is determined as the target injection point U. As a result, the permeation area S of the material to be administered which has been injected at the target injection point U more efficiently fills the abnormal region R' by injecting the material to be administered at the target injection point U. Incidentally, a region where the material to be administered is injected may be the low-motion region P (see FIG. 7A), which is the entire abnormal region R' including the infarct region Q (see FIG. 7B), or may be only the target region R (see FIG. 7C) excluding the infarct region Q from the low-motion region P. However, it is preferable to determine the target injection point U by focusing on the target region R (see FIG. 7C) rather than the infarct region Q in the low-motion region P (see FIG. 7A) which is the entire abnormal region R' if considering the spread of the permeation area S as described above.

The control unit 16 determines the order of the plurality of target injection points U. The control unit 16 creates the developed image including the abnormal region R' and the target injection point U, and causes the display unit 14 to display the developed image. Then, the control unit 16 causes the display unit 14 to display the plurality of target injection points U in a mode based on the determined order. For example, the control unit 16 causes the determined order to be written together with the target injection point U as illustrated in FIGS. 10A and 10B. For example, the control unit 16 displays only the target injection point U in the next order. The control unit 16 estimates a movement path V in which a distal end of the injection member that injects the material to be administered moves via the plurality of target injection points U, and determines the order of the target injection points U based on the movement path V. For example, the control unit 16 determines the order of the target injection points U such that the movement path V becomes the shortest. Specifically, the control unit 16 determines the target injection points U that are closest to each other in order. The control unit 16 may causes the display unit 14 to display the developed image on which the estimated movement path V is superimposed. As a result, an operator such as a medical worker can grasp the optimum way of moving the injection member according to the order of the target injection points U.

As illustrated in FIG. 10A, the control unit 16 may determine the order of the target injection points U such that the movement path V draws a spiral around a major axis O from the aortic valve AV (see FIGS. 7A to 7C) to the cardiac apex AP (see FIGS. 7A to 7C) in the left ventricle LV of the heart. As a result, the movement path V becomes a path that travels along a circumferential direction M from the aortic valve AV on the front side toward the cardiac apex AP on the back side without being turned back on the way in the left ventricle LV, and thus, the operation of the injection member can be facilitated.

As illustrated in FIG. 10B, the control unit 16 may determine the order of the target injection points U such that the movement path V reciprocates along the major axis O from the aortic valve AV to the cardiac apex AP in the left ventricle LV of the heart. As a result, the movement path V extends along the long axis O, and thus, it is possible to reduce a risk that the movement of the injection member is hindered by the papillary muscle located along the major axis O in the left ventricle LV, and it is possible to reduce catching on the chorda tendinea accompanying the mitral valve.

Figure 11:
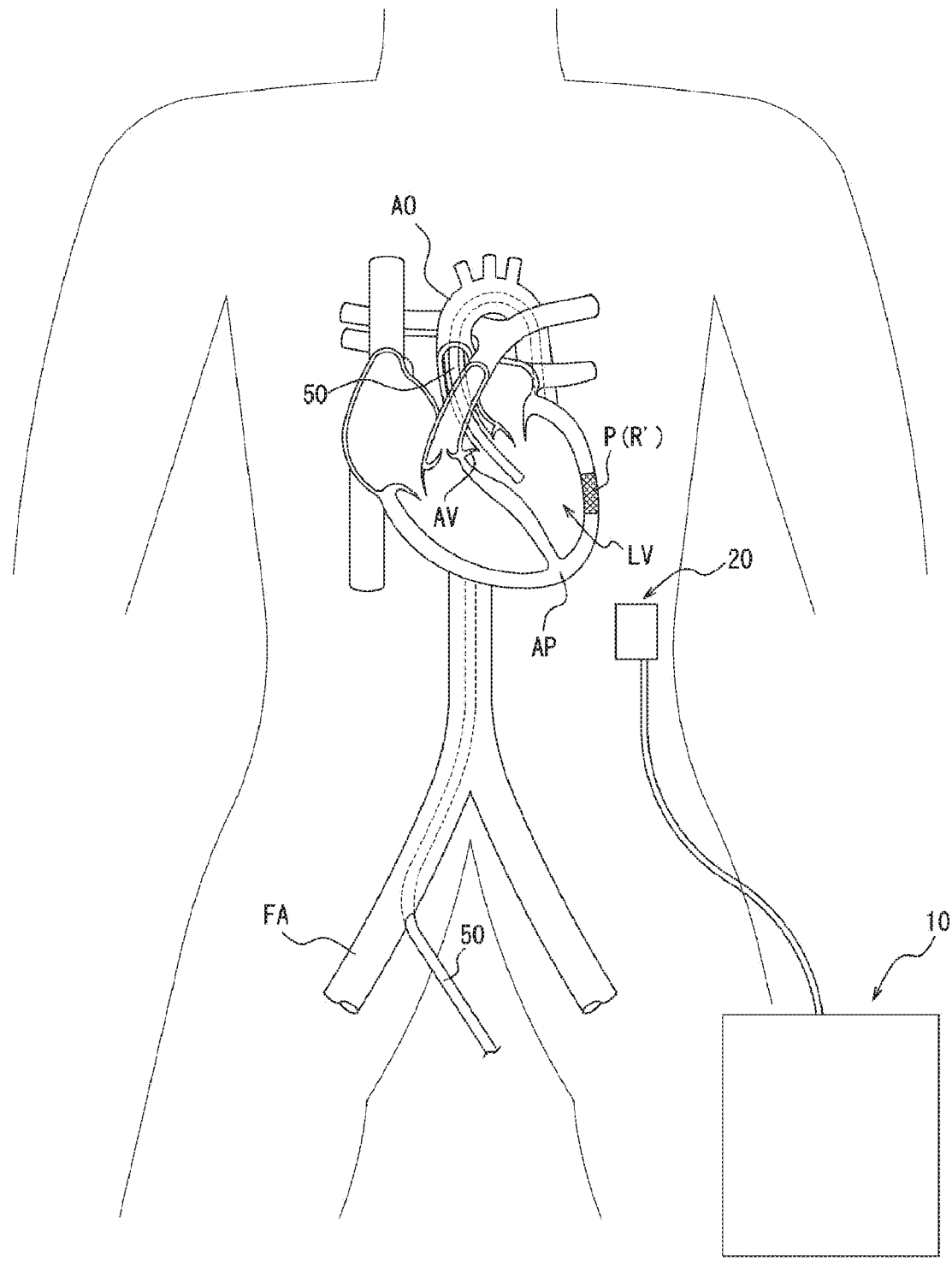
FIG. 11 is a view illustrating a state of a treatment using an injection member in accordance with embodiments of the present disclosure.

FIG. 11 is a view illustrating a state of the treatment by the injection member. FIG. 11 illustrates a state where a catheter 50 extends from a femoral artery FA through an aorta AO to the aortic valve AV which is the entrance of the left ventricle LV of the heart lumen. The infusion member is delivered through the catheter 50 to the left ventricle LV. Incidentally, the catheter 50 may extend from a radial artery of a wrist to the aortic valve AV, for example, without being limited to the extension from the femoral artery FA.

As illustrated in FIG. 11, the ultrasound image generation device 20 is located on the body surface of the subject, captures a first tomographic image as needed, and transmits the first tomographic image to the image processing device 10. In addition, the ultrasound image generation device 20 acquires position information of the distal end of the injection member as needed and transmits the position information to the image processing device 10. As a result, the control unit 16 of the image processing device 10 can cause the display unit 14 to display the developed image that follows the position of the distal end of the injection member, for example. In addition, the ultrasound image generation device 20 may be captured not only from the body surface but also from the esophagus, blood vessel, and heart lumen (atrium or ventricle). However, it is preferable that the ultrasound image generation device 20 capture the image from the body surface in terms that non-invasive treatment can be performed.

The control unit 16 may display the target injection point U which has been subjected to the injection treatment of the material to be administered using the injection member among the plurality of target injection points U on the developed image of the display unit 14 in a different mode from the target injection point U which has not been treated. The control unit 16 determines that the target injection point U has been treated based on, for example, an input of a signal indicating the completion of the treatment via the operation input unit 13. The control unit 16 may determine the treated target injection point U based on a newly input first tomographic image.

Since the image processing device 10 can determine the positions of a plurality of target injection points U through which the material to be administered needs to be injected into the abnormal region R' as described above, a more specific treatment simulation can be performed before performing the treatment. In addition, since the image processing device 10 displays the target injection point U in a mode based on the order in which the treatment needs to be performed, the treatment in a predetermined order can be guided to the operator. Furthermore, since the target region R including the hibernating myocardium and the stunned myocardium with a relatively high treatment effect is identified in advance in the abnormal region R', the target injection point U can be determined focusing on the position of the target region R, and the treatment effect can be improved.

Incidentally, the example in which the acquisition of the three-dimensional structure information of the heart and the injection into the heart wall of the material to be administered are performed in parallel has been described in FIGS. 4 to 11, it is not always easy to display and store the three-dimensional structure of the heart during the operation. For example, it is difficult to grasp even a complicated irregular structure such as the papillary muscle (medium column) inside the ventricle by intraoperative X-ray fluoroscopy. In addition, it is also conceivable to acquire the three-dimensional structure information of the heart using a three-dimensional ultrasound diagnostic device, but it is difficult to accurately grasp even the complicated irregular structure as described above. Therefore, it is also possible to consider a user mode, for example, in which three-dimensional structure information of a heart is acquired before an operation by a computed tomography device or a magnetic resonance imaging device, a developed image is generated based on the three-dimensional structure information, and an input of a treatment region is received from a medical worker while displaying the developed image on the display unit 14 during the operation. In this use mode, intra-cardiac monitoring during the operation can be performed with a conventional X-ray fluoroscopic image. That is, the medical worker can acquire detailed information such as a position and a size of the abnormal region R' in the heart and a position of the target injection point U from the developed image displayed on the display unit 14 and execute the operation while confirming the conventional X-ray fluoroscopic image. Then, when the operation input unit 13 (see FIG. 1 and the like) receives an input of a treatment region into which a material to be administered has been injected, the control unit 16 displays a developed image reflecting the treatment region on the display unit 14. Incidentally, the intraoperative monitoring of the heart is not limited to the above-described X-ray fluoroscopic image, and may be performed by, for example, a three-dimensional ultrasound diagnostic device. As described above, the three-dimensional structure information acquired by the image processing device 10 may be obtained in real time during the operation or may be obtained before the operation.

In the present embodiment, the image processing device 10 includes: the information input unit 11 that receives the input of the three-dimensional structure information indicating the three-dimensional structure of the heart; and the control unit 16 serving as the image generation unit that develops the inner wall of the atria and ventricles of the heart indicated by the three-dimensional structure information into the two-dimensional image based on the equal-area projection and generates the developed image interrupted by dividing the two-dimensional image into the front wall, the rear wall, the left wall, and the right wall of the inner wall as described above.

Since the inner wall of the atrium and ventricle of the heart is developed into the two-dimensional image based on the equal-area projection, it is possible to accurately grasp the size of the region of interest, the proportion in the inner wall, and the like. In addition, since the development is performed to be divided (split) into the front wall, the rear wall, the left wall, and the right wall of the atrium and ventricle of the heart, it is possible to intuitively grasp the relationship between each part on the developed image after the interruption and each of the front wall, rear wall, left wall, and right wall of the atrium and ventricle. As a result, it is possible to intuitively grasp positions of the region of interest and the treatment region in the atrium and ventricle. Therefore, the state of the inner wall of the heart can be intuitively and more accurately grasped.

In addition, the control unit 16 serving as the image generation unit makes the mode of the region of interest in the heart different from the mode of other regions on the developed image in the present embodiment. Although the region of interest is the infarcted region Q (see FIG. 7B), and the target region R (see FIGS. 1 and 7C) including the hibernating myocardium and the stunned myocardium in the present embodiment, the region of interest is not limited thereto, and, for example, only the infarct region Q, only the target region R, or the low-motion region P (see FIG. 7A) that does not distinguish the infarct region Q and the target region R may be set as the region of interest. The region of interest can be grasped intuitively and accurately on the developed image by making the mode of the region of interest different from other regions by, for example, mapping using different colors.

In addition, the control unit 16 serving as the image generation unit identifies the position of the heart valve based on the three-dimensional structure information, and maps the identified heart valve on the developed image in the present embodiment.

Since the heart valve that controls the entry and exit of blood into the atrium and ventricle is mapped on the developed image, it is possible to intuitively and more accurately grasp the region of interest and the treatment region.

Incidentally, the image processing device 10 can also be realized by a computer and a program although not specifically described in the embodiment. In addition, the program may be recorded on a computer readable medium. If a computer-readable medium is used, the program can be installed on a computer. Here, the computer-readable medium on which the program is recorded may be a non-transitory recording medium. The non-transitory recording medium is not particularly limited, and may be a recording medium such as a CD-ROM and a DVD-ROM. In addition, the program can also be provided through a network.

The present disclosure is not limited to the configuration identified by the above-described respective embodiments, and various modifications can be made within a scope not departing from a gist of the disclosure to be described in the claims. For example, functions included in the respective components, the respective steps, and the like can be rearranged so as not to have logical contradiction, and it is possible to combine or divide the plurality of components or steps into one.

DESCRIPTION OF REFERENCE CHARACTERS

1 Image processing system
10 Image processing device
11 Information input unit
12 Heartbeat input unit
13 Operation input unit
14 Display unit
15 Storage unit
16 Control unit (image generation unit)
20 Ultrasound image generation device
21 Ultrasound transmission unit
22 Ultrasound reception unit
23 Image formation unit
30 Radiation image generation device
31 Radiation emission unit
32 Radiation detection unit
33 Image formation unit
40 Heartbeat acquisition device
50 Catheter
AO Aorta
AP Cardiac apex
AV Aortic valve
BV Blood vessel
FA Femoral artery
LV Left ventricle
A Marker
B Heart valve
C Coronary artery
D Papillary muscle
M Circumferential direction
O Long axis
P Low-motion region
Q Infarct region
R Target region
R' Abnormal region
S Permeation area
T Injection point
U Target injection point
V Movement path

What is claimed is:

1. An image processing device comprising:
an information input unit comprising a communications interface that receives as an input three-dimensional structure information indicating a three-dimensional structure of a heart; and
an image generation unit comprising a processor that develops an inner wall of atria and ventricles of the heart indicated by the three-dimensional structure information into a two-dimensional image based on an equal-area projection and generates a developed image interrupted by dividing the two-dimensional image into a front wall, a rear wall, a left wall, and a right wall of the inner wall.

2. The image processing device of claim 1, wherein the processor of the image generation unit makes a mode of a region of interest in the heart different from a mode of another region on the developed image.

3. The image processing device of claim 2, wherein the communications interface of the information input unit receives as an input time-series three-dimensional structure information including diastole and systole of the heart, and
the processor of the image generation unit generates the developed image for each of the diastole and the systole based on the time-series three-dimensional structure information.

4. The image processing device of claim 3, wherein the region of interest is an infarcted region of the heart, and
the processor of the image generation unit corrects a position of the region of interest based on a developed image in the diastole and a developed image in the systole.

5. The image processing device of claim 1, wherein the processor of the image generation unit identifies a position of a heart valve based on the three-dimensional structure information, and maps the identified heart valve on the developed image.

6. The image processing device of claim 5, wherein the processor of the image generation unit displays an open/closed state of the heart valve on the developed image.

7. The image processing device of claim 1, wherein the processor of the image generation unit obtains a wall thickness of the inner wall based on the three-dimensional structure information, and maps the obtained wall thickness on the developed image.

8. The image processing device of claim 1, wherein the communications interface of the information input unit further receives as an input electrocardiogram information indicating an electrocardiogram of the inner wall, and
the processor of the image generation unit maps the electrocardiogram of the inner wall on the developed image based on the electrocardiogram information.

9. The image processing device of claim 1, wherein the processor of the image generation unit acquires a wall motion state of the inner wall based on the three-dimensional structure information, and maps the acquired wall motion state on the developed image.

10. The image processing device of claim 9, wherein the communications interface of the information input unit further receives as an input electrocardiogram information indicating an electrocardiogram of the inner wall, and
the processor of the image generation unit identifies a region where the wall motion state of the inner wall and the electrocardiogram of the inner wall satisfy predetermined conditions, and maps the identified region on the developed image.

11. The image processing device of claim 1, further comprising:
an operation input unit comprising a user interface that receives an operation input,
wherein the processor of the image generation unit displays the generated developed image on a display unit, and displays a marker indicating a position given in instruction by the operation input on the developed image in a superimposed manner when the user interface of the operation input unit receives the operation input giving an instruction on the position on the developed image displayed on the display unit.

12. The image processing device of claim 1, further comprising:
an operation input unit comprising a user interface that receives an operation input,
wherein the processor of the image generation unit displays the generated developed image on a display unit, obtains a wall thickness of the inner wall based on the three-dimensional structure information, and displays the wall thickness at a position given in instruction by the operation input on the display unit when the user interface of the operation input unit receives the operation input giving an instruction on the position on the developed image displayed on the display unit.

13. An image processing method, executed using an image processing device, the method comprising:
receiving, via a processor, as an input three-dimensional structure information indicating a three-dimensional structure of a heart; and
developing, via the processor, an inner wall of atria and ventricles of the heart indicated by the three-dimensional structure information into a two-dimensional image based on an equal-area projection; and
generating, via the processor, a developed image interrupted by dividing the two-dimensional image into a front wall, a rear wall, a left wall, and a right wall of the inner wall.

14. The image processing method of claim 13, further comprising:
identifying, via the processor, a position of a heart valve based on the three-dimensional structure information; and
mapping, via the processor, the identified heart valve on the developed image.

15. The image processing method of claim 14, wherein generating the developed image further comprises:
displaying, via the processor, an open/closed state of the heart valve on the developed image.

16. The image processing method of claim 15, further comprising:
obtaining, via the processor, a wall thickness of the inner wall based on the three-dimensional structure information; and
mapping, via the processor, the obtained wall thickness on the developed image.

17. The image processing method of claim 15, further comprising:
receiving; via the processor, as an input electrocardiogram information indicating an electrocardiogram of the inner wall; and mapping, via the processor, the electrocardiogram of the inner wall on the developed image based on the electrocardiogram information.

18. The image processing method of claim 15, further comprising:
acquiring, via the processor, a wall motion state of the inner wall based on the three-dimensional structure information; and
mapping, via the processor, the acquired wall motion state on the developed image.

19. The image processing method of claim 17, further comprising:
receiving, via the processor, as an input electrocardiogram information indicating an electrocardiogram of the inner wall;
identifying, via the processor, a region where the wall motion state of the inner wall and the electrocardiogram of the inner wall satisfy predetermined conditions; and
mapping, via the processor, the identified region on the developed image.

20. A non-transitory computer-readable medium having computer executable instructions stored thereon that, when executed by a processor, cause the processor to:
receive as an input three-dimensional structure information indicating a three-dimensional structure of a heart; and
develop an inner wall of atria and ventricles of the heart indicated by the three-dimensional structure information into a two-dimensional image based on an equal-area projection and generating a developed image interrupted by dividing the two-dimensional image into a front wall, a rear wall, a left wall, and a right wall of the inner wall.

* * * * *